United States Patent [19]
Schlinger et al.

[11] 4,242,234
[45] Dec. 30, 1980

[54] CATALYST FOR CONVERSION OF HYDROGEN AND CARBON MONOXIDE INTO $C_1$-$C_4$ RANGE HYDROCARBONS

[75] Inventors: Warren G. Schlinger, Pasadena; William L. Slater, LaHabra, both of Calif.

[73] Assignee: Texaco Inc., White Plains, N.Y.

[21] Appl. No.: 6,835

[22] Filed: Jan. 26, 1979

Related U.S. Application Data

[62] Division of Ser. No. 865,764, Dec. 29, 1977.

[51] Int. Cl.³ .......................... B01J 23/78; B01J 27/04
[52] U.S. Cl. .............................. 252/439; 260/449.6 R; 260/449.6 M
[58] Field of Search ................ 252/439, 443, 474; 260/449 M, 449 R, 449.6 M, 449.6 R

[56] References Cited

U.S. PATENT DOCUMENTS

| | | | |
|---|---|---|---|
| 2,485,945 | 10/1949 | Walker | 260/449.6 |
| 2,717,260 | 9/1955 | Davis et al. | 260/449.6 |
| 2,805,239 | 9/1957 | Rottig | 252/474 X |

OTHER PUBLICATIONS

Storch et al., *Fischer-Tropsch and Related Syntheses,* John Wiley, 1951, pp. 274-279.

*Primary Examiner*—W. J. Shine
*Attorney, Agent, or Firm*—Carl G. Ries; Albert Brent

[57] ABSTRACT

A process for conversion of hydrogen and carbon monoxide into hydrocarbons in the presence of an ebullient bed of catalyst comprising reduced iron oxide containing an amount of potassium equivalent to 2 to 10 pounds potassium carbonate per 1000 pounds iron oxide catalyst, and having an average particle size in the range of 100-1000 microns. The catalyst may be sulfided for increasing the yield of $C_1$-$C_4$ range hydrocarbons.

2 Claims, No Drawings

CATALYST FOR CONVERSION OF HYDROGEN AND CARBON MONOXIDE INTO $C_1$–$C_4$ RANGE HYDROCARBONS

This is a division of application Ser. No. 865,764, filed Dec. 29, 1977.

BACKGROUND OF THE INVENTION

The present invention relates to a process for converting hydrogen and carbon monoxide into hydrocarbon products. More particularly, the present invention relates to processes for conversion of hydrogen and carbon monoxide into $C_1$–$C_4$ range saturated hydrocarbons, particularly methane, in the presence of an iron based catalyst having improved activity and selectivity for production of $C_1$–$C_4$ range hydrocarbons from hydrogen and carbon monoxide.

Processes for production of gas streams comprising hydrogen and carbon monoxide from carbonaceous and/or hydrocarbon charge stocks are well known in the prior art. Of particular interest for providing hydrogen and carbon monoxide charge for the process of the present invention, is partial oxidation of hydrocarbons and/or carbonaceous charge stocks with a molecular oxygen-containing gas. Such partial oxidation processes are widely practiced on a commercial basis. In partial oxidation reactions, hydrocarbons or carbonaceous charge stocks, ranging from methane through coal or coke, are contacted with an amount of molecular oxygen insufficient for complete combustion of such charge stock, at temperatures in the range of about 1600° F. to about 3000° F. and pressures in the range of about 1–250 atmospheres, for conversion of the oxygen and charge stock into hydrogen and carbon monoxide. It is known to charge water or steam to partial oxidation reactions for increasing the ratio of hydrogen to carbon monoxide in the product gas. Also, it is known to maintain the reaction temperature within the range of about 1600°–2000° F. and to add water or steam to the partial oxidation reaction for production of a gas product comprising substantial amounts of methane as well as hydrogen and carbon monoxide. As no catalyst is employed in the partial oxidation reaction, it is not necessary to remove sulfur and other materials from the charge stock prior to the partial oxidation reaction. Sulfur is primarily converted to hydrogen sulfide ($H_2S$) and minor amounts of carbonyl sulfide (COS). In addition to hydrogen, carbon monoxide and methane, a minor portion of the hydrocarbon or carbonaceous charge stock is converted to carbon dioxide and about 0.5 to 5 weight percent is converted to soot. Processes for removal of impurities from partial oxidation effluent gases and production of gases substantially comprising hydrogen and carbon monoxide are well known in the prior art and are widely practiced.

The molar ratio of hydrogen to carbon monoxide in a product gas from a partial oxidation process may be increased substantially by subjecting such gas to the water gas shift reaction. The water gas shift reaction comprises heating the gas to a temperature of about 550° F. or higher and contacting said gas with steam in the presence of a suitable catalyst. Under such conditions, carbon monoxide reacts with steam to form carbon dioxide and hydrogen. Carbon dioxide formed from the water gas shift reaction may be removed from the product gas by acid gas absorption techniques.

It is becoming increasingly desirable to convert low value hydrocarbon and carbonaceous fuels into more useful fuel products, particularly methane and low molecular weight $C_1$–$C_4$ range saturated hydrocarbons. Particularly, it is desirable to convert hydrocarbonaceous or carbonaceous charge stocks containing high percentages of impurities such as ash and sulfur into clean products which may be burned as fuels without contributing substantial pollution of the environment. Partial oxidation processes produce product gasses comprising hydrogen and carbon monoxide which may be efficiently treated for removal of impurities which may lead to air pollution. However, the resulting gas products, substantially comprising hydrogen and carbon monoxide, have a relatively low heating value particularly when compared to naturally occurring fuel gases such as methane. Therefore, conversion processes for reacting hydrogen with carbon monoxide for conversion into low molecular weight saturated hydrocarbons, particularly methane, have been developed. In such processes hydrogen and carbon monoxide in a molar ratio of from about 1:1 to about 4:1 and preferably in the range of about 1:1 to about 3:1 are contacted at pressures in the range of about atmospheric to about 25 atmospheres and higher, and temperatures in the range of about 600° F. to about 900° F., in the presence of selected catalysts for conversion of hydrogen and carbon monoxide into low molecular weight saturated hydrocarbons. Catalysts which may be employed in such reactions include metals, preferably in subdivided form, such as iron, cobalt, nickel, vanadium, molybdenum, and tungsten, and compounds of these metals such as the halides, oxides, sulfides, molybdates, sulfates, or oxylates. Mixtures and other combinations of two or more of these metals and/or compounds of these metals may be employed as desired. Exemplary of such prior art processes for conversion of hydrogen and carbon monoxide is the process disclosed in U.S. Pat. No. 3,730,694, D. K. Wunderlich, issued May, 1973. In such processes, the heat of reaction from the conversion of hydrogen and carbon monoxide is substantial and means for removing such heat of reaction must be provided to prevent a rapid increase in temperature which, if uncontrolled, would damage the catalyst and/or damage the processing equipment. Methods for controlling the temperature in such conversion reactions, include recycling inert gasses, such as a portion of the product gas, and providing indirect heat exchange such as steam coils, within the catalyst bed. One known method for removing the heat of reaction and thereby controlling the conversion reaction temperature is to employ catalyst in finely subdivided form (less than 100 microns) and fluidizing said catalyst with gas charged to the process to form a dense phase fluidized bed. Heat exchange means, such as steam generation coils, are suspended within said fluidized bed for absorption of the heat of reaction. Such fluidized beds have very good heat transfer properties which allow rapid, even transfer of heat from the catalyst bed to the heat removal means, e.g., the steam coils.

The more reactive catalysts for conversion of hydrogen and carbon monoxide, particularly those containing nickel, are poisoned by sulfur and sulfur compounds. Such poisoning results in the catalysts losing activity for conversion of hydrogen and carbon monoxide. Whereas, catalysts which are more tolerant of sulfur, particularly iron containing catalysts, have lower initial activity for conversion of hydrogen and carbon monoxide. Therefore, in processes of the prior art, hydrogen and carbon monoxide charged to such conversion reactions are commonly treated for substantially complete removal of sulfur and sulfur compounds if a highly active nickel-based catalyst is to be employed. Otherwise, use of more sulfur tolerant catalysts results in lower conversion of hydrogen and carbon monoxide into desirable low molecular weight hydrocarbon compounds.

SUMMARY OF THE INVENTION

Now, according to the present invention, an improved process employing improved iron-containing catalysts is disclosed for converting hydrogen and carbon monoxide into low molecular weight saturated hydrocarbons. The improved catalysts have increased activity over iron-containing catalysts of the prior art, and have physical properties which allow efficient transfer of the heat of reaction from the catalyst to heat exchange means such as steam generation coils.

The process of the present invention comprises contacting hydrogen and carbon monoxide, in a molar ratio in the range of at least 1:1 to about 3:1 respectively, at a reaction temperature in the range of about 600° to 1000° F., a pressure in the range of about 200 to 3000 psig, and a space velocity in the range of about 250 to 2,500 standard volumes carbon monoxide plus hydrogen per hour per volume of catalyst (v/hr/v); in the presence of an ebullient bed of an improved iron-based catalyst.

In one embodiment of the present invention, the improved catalyst consists essentially of iron oxide selected from mill scale and/or magnetite ground to an average particle size in the range of about 100 to about 1000 microns (preferably 350-800 microns); wherein said ground iron oxide is treated with a water soluble potassium compound such as potassium carbonate in an amount sufficient to provide from about 2 to about 10 pounds of potassium (calculated as potassium carbonate) per 1000 pounds of iron oxide; wherein said potassium containing iron oxide is chemically reduced with hydrogen; and wherein said reduced catalyst is treated with sulfur, or a compound suitable for sulfiding the catalyst (e.g. $H_2S$), in an amount sufficient to provide said catalyst with a sulfur content in the range of about 0.01 to about 0.10 weight percent, (preferably about 0.022 to about 0.075 weight percent).

Advantages of the present invention include a process for conversion of hydrogen and carbon monoxide to low molecular weight saturated hydrocarbons in the $C_1$-$C_4$ range employing a sulfur-tolerant, iron-based catalyst having good heat transfer properties, and having improved activity over iron-based catalysts of the prior art. This and other advantages will be discussed in the detailed description which follows.

BRIEF DESCRIPTION OF THE DRAWING

FIG. 1 of the drawings is a graphical representation showing hydrogen and carbon monoxide conversion as a function of catalyst particle size for unsulfided catalysts of the present invention, at conditions of constant hydrogen-carbon monoxide molar ratio, temperature, pressure, and space velocity. Hydrogen and carbon monoxide conversion is shown at space velocities of 500 and 1500 v/hr/v.

FIG. 2 of the drawings is a graphical representation showing the increase in liquid product yield as a function of catalyst particle size for unsulfided catalysts of the present invention, at conditions of catalyst hydrogen-carbon monoxide molar ratio, temperature, pressure, and space velocity. Liquid product yield is shown at hydrogen plus carbon monoxide space velocities of 500 and 1500 v/hr/v.

FIG. 3 of the drawings is a graphical representation showing the increase in $C_1$-$C_4$ hydrocarbon yield, as a percentage of total yield, with increasing catalyst sulfur content, over the range disclosed herein.

DETAILED DESCRIPTION OF THE INVENTION

In the present invention, feed gas to the conversion reaction is a gas containing substantial amounts of hydrogen and carbon monoxide in molar ratio of at least 1:1 to about 3:1 respectively. Preferably, since the product of this conversion reaction is $C_1$-$C_4$ range saturated hydrocarbons, the feed gas is selected from products of such reactions as partial oxidation of relatively heavy hydrocarbons and/or carbonaceous materials. The feed gas may contain other materials, such as carbon dioxide and small amounts of hydrogen sulfide, as well as other hydrocarbons such as methane, ethane, propane and butanes. Preferably, a major portion of the feed gas will be made up of hydrogen, and carbon monoxide. Hydrogen is preferably present in the feed gas in a molar amount sufficient to react with all the carbon monoxide and unsaturated hydrocarbons present such that the hydrocarbon components of the reaction product will essentially comprise $C_1$-$C_4$ range hydrocarbons which are useful as clean burning fuels. The hydrogen to carbon monoxide molar ratio should be above 1:1 to prevent excess coke formation, but does not need be as high as 3:1, as might be inferred from the following equation:

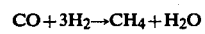

$$CO + 3H_2 \rightarrow CH_4 + H_2O$$

The iron-based catalyst of the present invention is a good carbon monoxide shift catalyst. So, if the system is deficient in hydrogen, some of the crbon monoxide will react with water present (either from the feed gas or produced in the reaction) to form additional hydrogen. Such additional hydrogen is available for reaction with carbon monoxide.

The reaction temperature favors formation of hydrogen, so the hydrogen to carbon monoxide molar ratio in effluent gas from the conversion reaction is appreciably greater than in the feed. Since the hydrogen to carbon monoxide molar ratio in the effluent gas from the conversion reaction is greater than in the feed, effluent gas may be recycled for increasing the hydrogen to carbon monoxide molar ratio in the conversion reaction. Preferably, at least a portion of the water and carbon dioxide reaction by-products are removed from the effluent gas prior to recycle. Water may be condensed from the effluent gas, and carbon dioxide may be removed by acid-gas absorption techniques, for example absorption into monoethanolamine or diethanolamine.

Impurities in the feed gas, such as hydrogen sulfide and carbonyl sulfide, may be conveniently removed by conventional absorption techniques such as absorption into monoethanolamine, diethanolamine, etc. Complete removal of such impurities is not required, and if they comprise only a small proportion of the feed gas, removal will be unnecessary. As will be discussed in detail below, sulfur reacted with the iron-based catalyst of the present invention improves selectivity for conversion of hydrogen and carbon monoxide to low molecular weight saturated hydrocarbons. Preferably, carbon dioxide comprises less than 2 mole percent of the feed gas to the conversion reaction.

Iron-based catalysts of the present invention are prepared from iron oxide selected from magnetite and/or mill scale ground and screened to an average particle size distribution in the range of about 100–1000 microns. Such particle size distribution is critical in preparing the improved catalysts of the present invention, as catalysts of smaller particle size show substantially reduced activity for conversion of hydrogen and carbon monoxide. Catalysts having particle sizes larger than about 1000 microns do not have substantially greater activity, and are difficult to maintain in a fluidized or ebullient condition, which difficulty leads to problems in transferring the large amount of exothermic heat of the conversion reaction from the catalyst bed to heat exchange means, such as steam generation coils.

The ground and screened magnetite and/or mill scale is impregnated with a water solution of a potassium compound, such as potassium carbonate, in an amount sufficient to provide from about 2 pounds to about 10 pounds, and preferably about 7 pounds, of potassium carbonate per 1000 pounds of iron oxide. Upon drying, the potassium impregnated magnetite and/or mill scale is chemically reduced by contacting with molecular hydrogen at an elevated temperature and pressure. Hydrogen, flowing at a superficial vapor velocity of about 0.1 to about 2 ft/sec, having a pressure of about 100 to 1000 psig, is contacted with the potassium-impregnated iron oxide at a temperature in the range of about 650°–800° F. for a time sufficient to reduce chemically a substantial portion of the magnetite and/or mill scale.

Upon impregnation with potassium and reduction with hydrogen, the catalyst is useful in a Fischer-Tropsch reaction for conversion of hydrogen and carbon monoxide into olefins, higher molecular weight hydrocarbons, alcohols and organic acids, without further treatment or conditioning steps. In such a Fisher-Tropsch reaction, however, the yield of saturated $C_1$–$C_4$ range hydrocarbons is quite low.

According to the present invention, we have discovered that treating the potassium-containing, reduced iron catalyst with sulfur results in a catalyst having substantially improved selectivity for production of $C_1$–$C_4$ range hydrocarbons from conversion of hydrogen and carbon monoxide. Employing such catalyst in the critical size range of 100–1000 microns as discussed above, results in improved conversion rates for hydrogen and carbon monoxide compared to iron catalysts of the prior art.

In the present invention, the potassium containing reduced iron catalyst may be sulfided prior to use in a hydrogen and carbon monoxide conversion process, or may be sulfided during such conversion process. For sulfiding, the potassium-containing reduced iron catalyst is contacted with a compound capable of sulfiding the catalyst at an elevated temperature in the range of about 200° F. to about 900° F. in an amount and for a time sufficient to result in a sulfided catalyst containing from about 0.01 to about 0.1 weight percent sulfur, and preferably containing from about 0.022 to about 0.075 weight percent sulfur. Sulfur compounds suitable for treating the catalyst include hydrogen sulfide, mercaptans, and other compounds capable of sulfiding the catalyst.

The improved sulfided catalyst of the present invention, in the size range disclosed herein, is useful in reactions for converting hydrogen and carbon monoxide into high yields of $C_1$–$C_4$ range saturated hydrocarbons. Such conversion reactions are operated at temperatures in the range of about 600°–1000° F. preferably 650°–800° F., and pressures in the range of about 200–3000 psig, preferably 400–1500 psig. Formation of saturated hydrocarbons is favored by higher pressures, such that use of higher pressures, consistent with structural limitations of process equipment, is desirable. In the conversion reaction a fresh feed gas stream comprising hydrogen and carbon monoxide having hydrogen to carbon monoxide molar ratio of at least 1:1 to about 3:1, is contacted with the catalyst of the present invention at operating conditions including space velocities of about 250 to 2,500 SCF hydrogen plus carbon monoxide per hour per cubic foot of catalyst (v/hr/v), (preferably about 500 to 1500 (v/hr/v). Effluent gas from the conversion reaction is relatively richer in hydrogen, compared to carbon monoxide, i.e. the effluent gas has a higher $H_2/CO$ ratio than the feed gas. Preferably, a portion of this effluent gas is recycled to the conversion reaction for increasing the molar ratio of hydrogen to carbon monoxide in the reaction zone, and for improving overall conversion of hydrogen and carbon monoxide. Recycle ratios of about 0.5:1 to about 2:1, or higher, volumes recycle gas per volume of feed gas may be employed in the conversion reaction. The conversion reaction effluent gas contains substantial amounts of carbon dioxide and water as well as hydrocarbons, and unconverted hydrogen and carbon monoxide. It is preferred to treat the effluent gas for removal of liquid hydrocarbons, carbon dioxide and water prior to recycle to the conversion reaction.

The hydrogen and carbon monoxide conversion reaction contemplated herein is exothermic. Large amounts of the heat of reaction must be removed from the reaction zone. Within contemplation of the present invention, the improved catalyst, having average particle sizes in the 100–1000 micron range, is maintained in a vertical reactor vessel to provide a catalyst bed height in the range of 5 to 30 feet, preferably 10 to 25 feet. The feed and recycle gasses are charged to the bottom of the reactor vessel at a rate sufficient to provide a superficial vapor velocity in the range of about 1 to 10 feet per second, such that the bed of catalyst is expanded and maintained in an ebullient condition by the upward flowing gasses. Such ebullition provides excellent heat transfer throughout the catalyst bed, preventing hot spots and aiding transfer of the heat of reaction from all parts of the bed to the heat exchange means. For ebullient beds such as these, wherein large heats of reaction must be removed, heat exchange means comprising steam generation tubes or coils are very useful. Vertical tubes for generating steam are particularly useful for removing heat from the conversion reaction. Within the operating ranges of the conversion reaction disclosed herein, it has been found that vertical steam generating tubes in number sufficient to provide from about 2.5 to about 3.5 square feet of tube surface per cubic foot of ebullient catalyst are sufficient to remove the heat of reaction from the catalyst bed.

EXAMPLE I

To demonstrate the effect of particle size upon catalyst conversion activity and selectivity, a series of runs were performed employing catalysts of various average particle sizes for conversion of hydrogen and carbon monoxide into useful products.

The catalysts were prepared by grinding magnetite ore in a hammer mill, in separate grinding steps, to produce samples of ground ore having average particle sizes respectively 50, 100, 200, 400 and 800 microns. Each sample of ground ore was subjected to magnetic separation for removal of extraneous mineral matter present in the ore. Each sample of separated magnetite was treated with an aqueous solution of $K_2CO_3$ in an amount sufficient to provide about 7 pounds of $K_2CO_3$ per 1000 pounds of magnetite, and the treated magnetite was chemically reduced by contact with hydrogen, at a temperature of about 650° F. a pressure of about 200 psig, a hydrogen superficial vapor velocity of about 0.8 ft/sec, for a period of about 12–15 hours, until evolution of water ceased. For this example, the catalyst was not sulfided prior to use in the conversion reaction.

The reduced catalyst samples were then employed in processes for conversion of hydrogen and carbon monoxide into higher molecular weight products. In each of the conversion processes, a sample of catalyst of selected average particle size was loaded into an ebullient bed reactor in an amount sufficient to provide an ebullient catalyst bed height of about 23 ft. The exothermic heat of the hydrogen and carbon monoxide conversion reactions was removed from the reactor ebullient bed by indirect heat exchange with water contained in vertical pipes suspended within the reactor. The reactor ebullient bed temperature was controlled by controlling the pressure (and consequently the temperature) of steam generated within the vertical pipes suspended in the reactor.

A series of reaction runs were performed with each unsulfided catalyst sample, wherein the space velocity of hydrogen and carbon monoxide was varied in the range of 500–1500 volumes hydrogen plus carbon monoxide per hour per volume of catalyst, while reaction temperature, pressure, and gas recycle ratio were maintained constant. In each run, for each catalyst sample, reaction temperature was about 660° F., reaction pressure was about 414 psig, and recycle volume ratio was about one volume recycle gas per volume fresh hydrogen plus carbon monoxide feed gas. The molar ratio of hydrogen to carbon monoxide in the fresh feed gas was 2:1.

In each run, fresh hydrogen plus carbon monoxide, in a molar ratio of about 2:1 respectively was combined with recycle gas (described below) and was flowed into the bottom of the reactor vessel at a temperature of about 200° F. Within the reactor vessel, the up-flowing gasses contacted the catalyst bed under conditions for conversion of hydrogen and carbon monoxide at superficial vapor velocities such that the catalyst was expanded into an ebullient bed (and for smaller particle size catalyst the bed was fluidized). The exothermic heat of hydrogen and carbon monoxide conversion was transferred by indirect heat exchange into the vertical tubes wherein steam was generated at a controlled pressure for maintaining the temperature of the ebullient catalyst bed at about 660° F. The temperature throughout the ebullient bed was substantially constant and hot spots were avoided. Effluent gas comprising conversion products and unreacted hydrogen and carbon monoxide was continuously removed, free of entrained catalyst, from the top of the reactor vessel and was cooled in a condenser to condense normally liquid hydrocarbon, organic chemicals and water. The cooled reactor effluent was separated into a gas phase comprising light hydrocarbons, carbon dioxide, and unreacted hydrogen and carbon monoxide, and a liquid phase comprising normally liquid hydrocarbons, organic chemicals, and water. A portion of the gas phase equal in volume to the fresh hydrogen and carbon monoxide feed was returned to the reactor as recycle gas. The remaining portion of the gas phase, comprising light hydrocarbons and unreacted hydrogen and carbon monoxide was analyzed to determine the overall conversion of hydrogen and carbon monoxide within the reactor.

The liquid phase was analyzed to determine total yield of liquid hydrocarbons and organic chemicals based upon fresh hydrogen and carbon monoxide charge to the reactor.

Batches of each catalyst, having average particle sizes of 50, 100, 200, 400 and 800 microns, were employed in hydrogen and carbon monoxide conversion reactions as described above, at space velocities of 500 and 1500 SCF hydrogen plus carbon monoxide per hour per cubic foot of catalyst. Molar conversion of hydrogen and carbon monoxide and yields of liquid hydrocarbons and organic chemicals were determined for each catalyst sample at each space velocity. Results of these experimental conversion reactions are shown in FIG. 1 and FIG. 2 attached to this specification.

In FIG. 1, the conversion of hydrogen and carbon monoxide is expressed as percent conversion, e.g., $$\% \text{ conv.} = \frac{\text{fresh}(H_2 + CO) + \text{recycle}(H_2 + CO) - \text{effluent}(H_2 + CO)}{\text{fresh}(H_2 + CO) + \text{recycle}(H_2 + CO)} \times (100)$$

Percent conversion is plotted versus catalyst particle size for reaction space velocities of 500 v/hr/v and 1500 v/hr/v. As can be seen in FIG. 1, the percentage conversion of hydrogen and carbon monoxide increased as average particle size increased, within the range of about 50 to 800 microns. A projection of the catalyst activity curves in FIG. 1 indicates that catalyst activity does not increase further with an increase in particle size above about 1000 microns. This result is surprising and unexpected, for it is commonly believed that catalyst activity increases with increased catalyst surface area, and that surface area increases with decreasing particle size. This is the first indication that catalyst having large average particle size is more active than the same catalyst having a smaller average particle size.

In FIG. 2, data from the experimental runs is plotted to show liquid product yield versus unsulfided catalyst average particle size for space velocities of 500 and 1500 v/hr/v, with other reaction conditions held constant. The liquid product yield is expressed as barrels (42 gal) liquid products per MCF hydrogen plus carbon monoxide charge to the process. The liquid product comprises $C_3$ and heavier hydrocarbons and organic chemicals formed in the conversion reaction. As can be seen from FIG. 2, the liquid product yield increased, at constant space velocity and other operating conditions, as the catalyst average particle size increased within the range of 50–800 microns. At otherwise the same operating conditions, the curves of FIG. 2 demonstrate that, as the catalyst particle size increases within the range of 50–800 microns, that the liquid yield from hydrogen and carbon monoxide converted actually increases. Thus, not only is the catalyst activity increased with increased average particle size, but the selectivity of conversion to liquid products increases.

Thus, the results of the experiment for conversion of hydrogen and carbon monoxide into useful hydrocarbon and organic chemical products indicate that use of the conversion catalyst of this invention, having an average particle size in the range of about 100–1000 microns, and preferably in the range of about 350–800 microns, results in increased conversion of hydrogen and carbon monoxide and results in increased useful products from the conversion reaction. These results are surprising and unexpected, for it is commonly thought that increased catalyst particle size generally results in decreased catalyst area which contributes to decreased conversion activity. The observed increase in liquid yield, as catalyst particle size is increased, is likewise surprising and unexpected.

EXAMPLE 2

The following experiment was performed for conversion of hydrogen and carbon monoxide to demonstrate the effectiveness of sulfiding the reduced iron catalysts of the present invention for increasing the yield of $C_1$–$C_4$ range hydrocarbons at the expense of normally liquid hydrocarbons and organic chemicals.

As in Example 1, a magnetite ore was ground in a hammer mill to produce a sample having 350 micron average particle size. The ground magnetite was subjected to magnetic separation for removal of extraneous mineral matter present in the ore. The separated magnetite was treated with an aqueous solution of potassium carbonate in an amount sufficient to provide about 7 pounds of potassium carbonate per 1000 pounds of magnetite, and the treated magnetite was dried.

The potassium carbonate treated magnetite was loaded into an ebullient bed reactor, containing steam generation tubes for heat removal, wherein the magnetite was chemically reduced by contact with hydrogen at a temperature of about 650° F., a hydrogen superficial vapor velocity of about 0.8 ft/sec, for a period about 12–15 hours until evolution of water ceased.

After reduction, the resulting unsulfided catalyst was employed in a hydrogen and carbon monoxide conversion reaction to obtain product yields for comparison with yields obtained with the catalyst in a sulfided condition, which is described below. Operating conditions and results of this comparison run with unsulfided catalyst are shown as Run 1 in the Table below.

Upon completion of Run 1, hydrogen sulfide was introduced into the reaction zone with the hydrogen and carbon monoxide reactants under reaction conditions for sulfiding the catalyst. Hydrogen sulfide addition was continued until the catalyst contained 0.029 wt.% sulfur. The sulfided catalyst was then employed in a hydrogen and carbon monoxide conversion reaction for production of increased amounts of saturated $C_1$–$C_4$ range hydrocarbons. Operating conditions and results of this reaction with sulfided catalyst are shown as Run 2 in the Table below.

In the hydrogen and carbon monoxide conversion reactions of this example, the catalyst in the reactor vessel was expanded by upflowing charge gas to form an ebullient bed of about 23 ft. height. The exothermic heat of the conversion reaction was removed from the ebullient bed by indirect heat exchange with steam generated within steam tubes suspended within the reactor vessel.

In Runs 1 and 2, hydrogen plus carbon monoxide space velocity, reaction temperature, reaction pressure and gas recycle ratio were maintained about constant. Recycle gas was obtained by cooling the effluent gas from the reaction zone in a condenser to condense normally liquid hydrocarbon, organic chemicals, and water. The cooled reactor effluent was separated into a gas phase comprising light hydrocarbons, carbon dioxide, and unreacted hydrogen and carbon monoxide and a liquid phase comprising normally liquid hydrocarbons, organic chemicals, and water. A portion of the gas phase equal in volume to the fresh hydrogen and carbon monoxide feed gas was returned to the reactor as recycle gas. Composition analyses of fresh hydrogen and carbon monoxide feed, recycle gas, product gas and product liquid were performed to determine product yields for Runs 1 and 2 respectively.

TABLE

| RUN NUMBER | 1 | 2 |
|---|---|---|
| Catalyst: particle size, microns | 350 | 350 |
| Sulfur, wt. % | -0- | 0.029 |
| $H_2$ + CO fresh feed, | | |
| mol. % $H_2$ | 36.5 | 36.5 |
| mol. % CO | 40.5 | 40.5 |
| Inlet pressure, psig | 419 | 416 |
| Temperature, °F. | 663 | 655 |
| Recycle Ratio | 0.97/1 | 0.89/1 |
| $H_2$ + CO space velocity (v/hr/v) | 748 | 771 |
| Fresh feed rate, SCFH | 12,040 | 12,511 |
| Wet gas rate, SCFH | 2,998 | 4,242 |
| Conversion, % CO | 95.85 | 94.41 |
| % $H_2$ | 86.82 | 82.27 |
| % $H_2$ + CO | 90.29 | 86.41 |
| Yield $C_1$+ hydrocarbons and organic chemicals | | |
| lb prod/MCF $H_2$ + CO charge | 11.664 | 9.974 |
| lb prod/MCF $H_2$ + CO converted | 12.918 | 11.489 |
| Product distribution, wt. % of $C_1$+ | | |
| $CH_4$ | 8.61 | 19.49 |
| $C_2H_4$ | 4.91 | 2.66 |
| $C_2H_6$ | 2.65 | 12.83 |
| $C_3H_6$ | 8.38 | 8.94 |
| $C_3H_8$ | 1.13 | 6.48 |
| $C_4H_8$ | 7.05 | 9.60 |
| $C_4H_{10}$ | 1.62 | 3.38 |
| $C_5$ hydrocarbons | 51.56 | 32.61 |
| Alcohols | 10.40 | 3.07 |
| Acids | 3.68 | 0.95 |
| $C_1$–$C_4$ hydrocarbons | 34.35 | 63.38 |
| $C_5$+ hydrocarbon distillation, Vol. % | | |
| 400° F. E.P. naphtha | 79.0 | 87.7 |
| 400°/500° F. gas oil | 11.3 | 4.4 |
| 550° F.+ fuel oil | 8.0 | 5.2 |
| Polymer tar | 1.7 | 2.7 |

From examination of the operating conditions and results of Runs 1 and 2 shown in Table I, it can be seen that using the sulfided catalyst of the present invention (0.029 wt. percent sulfur) in a hydrogen and carbon monoxide conversion reaction (Run 2) results in product yield containing substantially more $C_1$–$C_4$ range hydrocarbons than the product yield from a conversion reaction (Run 1) employing unsulfided catalyst. Further, the amount of heavier hydrocarbons and organic chemicals (e.g. alcohols and acids) are substantially reduced when sulfided catalyst is employed. Consequently, the amount of gaseous $C_1$–$C_4$ range hydrocarbons useful as fuel gas is substantially increased when the sulfided catalyst of the present invention is employed.

EXAMPLE 3

A hydrogen plus carbon monoxide conversion reaction was performed using an initially unsulfided catalyst and process operating conditions as described above for Run 1 of Example 2. The fresh hydrogen and carbon monoxide feed gas, in the present example, contained about 0.05 vol. percent hydrogen sulfide, thus the catalyst was gradually sulfided by reaction with a portion of the hydrogen sulfide. During operation of the process of this example, samples of effluent gas and samples of catalyst were taken from time to time. The effluent gas samples were analyzed to determine conversion of hydrogen and carbon monoxide into $C_1$-$C_4$ range hydrocarbons, and corresponding catalyst samples were analyzed to determine the degree to which the catalyst had been sulfided. Operation of the process of this Example 3 was continued until essentially all the hydrocarbons formed were in the $C_1$-$C_4$ range. Thus at a sulfur content of about 0.073 weight percent in the catalyst, essentially 100% of the hydrocarbon products were $C_1$-$C_4$ saturated hydrocarbons. Hydrogen plus carbon monoxide conversion remained substantially the same at about 86 percent throughout the Experiment.

FIG. 3 is a plot of data obtained in this Example 3 to show the effect of sulfur upon the selectivity of the catalyst of the present invention for production of $C_1$-$C_4$ range hydrocarbons. As shown in FIG. 3, the methane yield increased linearly at constant operating conditions, from about 10.3 wt. percent methane in product gas at about 0 wt.% sulfur on catalyst to about 25 wt. percent methane in product gas at about 0.073 wt. percent sulfur on catalyst. The curves of FIG. 3 also demonstrate that, as the sulfur content of the catalyst increases in the range of 0 to about 0.073 wt.%, the weight ratio of gaseous hydrocarbons ($C_1$-$C_4$) to total hydrocarbons ($C_1$+) increases from about 40 wt.% $C_1$-$C_4$ hydrocarbons at 0 wt. percent sulfur on catalyst to essentially 100 wt. percent at about 0.073 wt. percent sulfur on catalyst.

EXAMPLE 4

A mill-scale is ground in a hammer mill to produce a sample having 350 micron average particle size. The ground mill scale is treated with an aqueous solution of potassium carbonate in an amount sufficient to provide about 7 pounds of potassium carbonate per 1000 pounds of mill scale, and the treated mill scale is dried.

The potassium carbonate treated mill scale is loaded in an ebullient bed reactor vessel containing steam generation coils for heat removal, wherein the treated mill scale is reduced by contact with hydrogen at a temperature of about 650° F., a hydrogen superficial vapor velocity of about 0.8 ft/sec, for a period until evolution of water ceases.

After chemical reduction, the unsulfided catalyst is treated with hydrogen and carbon monoxide containing a small amount of hydrogen sulfide under conditions for sulfiding the catalyst. Hydrogen sulfide addition is continued until the catalyst contains 0.075 wt. percent sulfur. The sulfided catalyst is then employed in a hydrogen and carbon monoxide conversion reaction under operating conditions and recycle ratios of Run 1 in Example 2 for production of increased amounts of $C_1$-$C_4$ range hydrocarbons. Under such operating conditions, conversion of hydrogen and carbon monoxide is about 90 percent, and essentially all the hydrocarbon conversion products consist of $C_1$-$C_4$ range hydrocarbons. Methane content of the product hydrocarbon gas is about 25 vol.% on a carbon dioxide and water free basis. Essentially no organic chemicals, such as alcohols and acids are formed in the reaction.

It is to be understood that modifications and variations of the process disclosed in the foregoing specification will occur to those skilled in the art, which modifications and variations are within the spirit and scope of the present invention. Consequently, the only limitations of the present invention intended are those included in the appended claims.

We claim:

1. An ebullient bed catalyst for producing from the product gas from the partial oxidation of hydrocarbon and/or carbonaceous materials light hydrocarbon gases containing an increased yield of $C_1$ to $C_4$ range saturated hydrocarbons essentially comprising: iron oxide selected from the group consisting of mill scale, magnetite, and mixtures thereof ground to an average particle size in the range of from about 350 to 800 microns, magnetically separated from extraneous matter, treated with an aqueous solution of potassium carbonate in an amount sufficient to deposit upon said ground iron oxide about 2-10 pounds potassium carbonate per 1000 pounds of iron oxide, dried, chemically reduced with hydrogen at a temperature in the range of about 650°-800° F. and a pressure in the range of about 100 to 1000 psig until evolution of water ceases, and then sulfided at an elevated temperature in the range of about 200°-900° F. with a sulfur-containing compound capable of sulfiding said catalyst such that said reduced iron catalyst contains from about 0.01 to about 1.0 weight percent sulfur.

2. An ebullient bed catalyst for producing from the product gas from the noncatalytic partial oxidation of hydrocarbon and/or carbonaceous material comprising $H_2$ and CO and containing $H_2S$ and COS, light hydrocarbon gases containing an increased yield of $C_1$ to $C_4$ range saturated hydrocarbons, said catalyst comprising: iron oxide selected from the group consisting of mill scale, magnetite and mixtures thereof, ground to a particle size of about 350 microns, magnetically separated from extraneous matter, treated with an aqueous solution of potassium carbonate in an amount sufficient to deposit upon said ground iron oxide about 2-10 pounds potassium carbonate per 1000 pounds iron oxide, dried, chemically reduced with hydrogen at a temperature in the range of about 650°-800° F. and a pressure in the range of about 100 to 1000 psig until evolution of water ceases, and subsequently sulfided at an elevated temperature in the range of about 200°-900° F. with a sulfur-containing compound capable of sulfiding said catalyst such that said reduced iron catalyst contains from about 0.022 to about 0.075 weight percent sulfur.

* * * * *